United States Patent [19]

Wolf, Jr. et al.

[11] Patent Number: 5,030,203
[45] Date of Patent: Jul. 9, 1991

[54] AMPULE FOR CONTROLLED ADMINISTRATION OF BENEFICIAL AGENT

[75] Inventors: L. Wolf, Jr., Crystal Lake; Rich Goldhaber, Lake Forest; Daniel R. Lynn, Lake Villa; Naomi L. Weinless, Highland Park, all of Ill.

[73] Assignee: Baxter International Inc., Deerfield, Ill.

[21] Appl. No.: 121,001
[22] Filed: Nov. 16, 1987
[51] Int. Cl.⁵ ............................................ A61M 37/00
[52] U.S. Cl. ..................................... 604/85; 604/56; 604/92; 604/890.1
[58] Field of Search .............. 604/56, 92, 890, 892, 604/82–85, 4, 6, 416, 251, 252, 262, 185; 424/467, 479

[56] References Cited

U.S. PATENT DOCUMENTS

| | | | |
|---|---|---|---|
| 25,129 | 2/1962 | Walter | 604/263 |
| 229,049 | 11/1973 | Roberts | 424/467 |
| 1,365,183 | 1/1921 | Moffatt | 604/85 |
| 2,612,160 | 9/1952 | Barr | 128/214 |
| 3,208,639 | 9/1965 | Marwell et al. | 222/82 |
| 3,760,984 | 9/1973 | Theeuwes | 222/95 |
| 3,845,770 | 11/1974 | Theeuwes et al. | 128/260 |
| 3,874,384 | 4/1975 | Diendoerter et al. | 604/408 |
| 3,993,066 | 11/1976 | Virag | 604/56 |
| 3,995,631 | 12/1976 | Higuchi et al. | 128/260 |
| 4,086,924 | 5/1978 | Latham | 604/6 |
| 4,087,363 | 5/1978 | Rosemeyer et al. | 210/315 |
| 4,111,202 | 9/1978 | Theeuwes | 128/260 |
| 4,130,647 | 12/1978 | Taylor | 514/254 |
| 4,134,943 | 1/1979 | Knitsch et al. | 424/467 |
| 4,235,236 | 11/1980 | Theeuwes | 604/892 |
| 4,257,426 | 3/1981 | Bailey | 604/92 |
| 4,381,776 | 5/1983 | Latham | 604/56 |
| 4,395,260 | 6/1983 | Todd et al. | 604/252 |
| 4,424,056 | 1/1984 | Urquhart et al. | 604/56 |
| 4,432,754 | 2/1984 | Urquhart et al. | 604/56 |
| 4,432,756 | 2/1984 | Urquhart et al. | 604/80 |
| 4,439,183 | 3/1984 | Theeuwes | 604/85 |
| 4,465,471 | 8/1984 | Harris et al. | 604/56 |
| 4,474,574 | 10/1984 | Wolfe et al. | 604/85 |
| 4,479,793 | 10/1984 | Urquhart et al. | 604/85 |
| 4,479,794 | 10/1984 | Urquhart et al. | 604/85 |
| 4,484,909 | 11/1984 | Urquhart et al. | 604/82 |
| 4,493,702 | 1/1985 | Urquhart et al. | 604/80 |
| 4,511,351 | 4/1985 | Theeuwes | 604/56 |
| 4,511,352 | 4/1985 | Theeuwes et al. | 604/56 |
| 4,511,353 | 4/1985 | Theeuwes | 604/85 |
| 4,515,585 | 5/1985 | Urquhart et al. | 604/85 |
| 4,521,211 | 6/1985 | Theeuwes | 604/85 |
| 4,533,348 | 8/1985 | Wolfe et al. | 604/85 |
| 4,534,757 | 8/1985 | Geller | 604/85 |
| 4,534,758 | 8/1985 | Akers et al. | 604/85 |
| 4,548,598 | 10/1985 | Theeuwes | 604/85 |
| 4,548,599 | 10/1985 | Urquhart et al. | 604/85 |
| 4,552,555 | 11/1985 | Theeuwes | 604/56 |
| 4,552,556 | 11/1985 | Urquhart et al. | 604/80 |
| 4,573,967 | 3/1986 | Hargrove et al. | 604/56 |
| 4,589,867 | 5/1986 | Israel | 604/85 |
| 4,623,334 | 11/1986 | Riddell | 604/51 |
| 4,685,918 | 8/1987 | Amidon et al. | 604/892.1 |
| 4,738,668 | 4/1988 | Bellotti et al. | 604/905 |
| 4,753,800 | 6/1988 | Mozda | 424/440 |
| 4,758,430 | 7/1988 | Sabin | 514/23 |
| 4,769,318 | 9/1988 | Hamasaki et al. | 424/101 |

FOREIGN PATENT DOCUMENTS

| | | | |
|---|---|---|---|
| 59684 | 9/1982 | European Pat. Off. | 604/56 |
| 0059694 | 9/1982 | European Pat. Off. | |
| 1108782 | 1/1956 | France | 604/251 |
| WO86/03416 | 6/1986 | PCT Int'l Appl. | |
| 497181 | 11/1970 | Switzerland | |
| 982107 | 2/1965 | United Kingdom | |

OTHER PUBLICATIONS

Myhre et al, Preservation of Red Cell antigens during storage of blood with different antigens; 1984.

Primary Examiner—C. Fred Rosenbaum
Assistant Examiner—Mark O. Polutta
Attorney, Agent, or Firm—Paul C. Flattery; Bradford R. L. Price; Paul E. Schaafsma

[57] ABSTRACT

An ampule defines a pair of opposed, flexible sides, sealingly enclosing a space which contains a mass of beneficial agent which is soluble in aqueous solution. Inlet and outlet ports communicate between the space and the exterior. Flow promoting means are positioned between the mass of beneficial agent and at least one opposed, flexible side to facilitate the formation of a fluid flow path along the mass of beneficial agent.

15 Claims, 2 Drawing Sheets

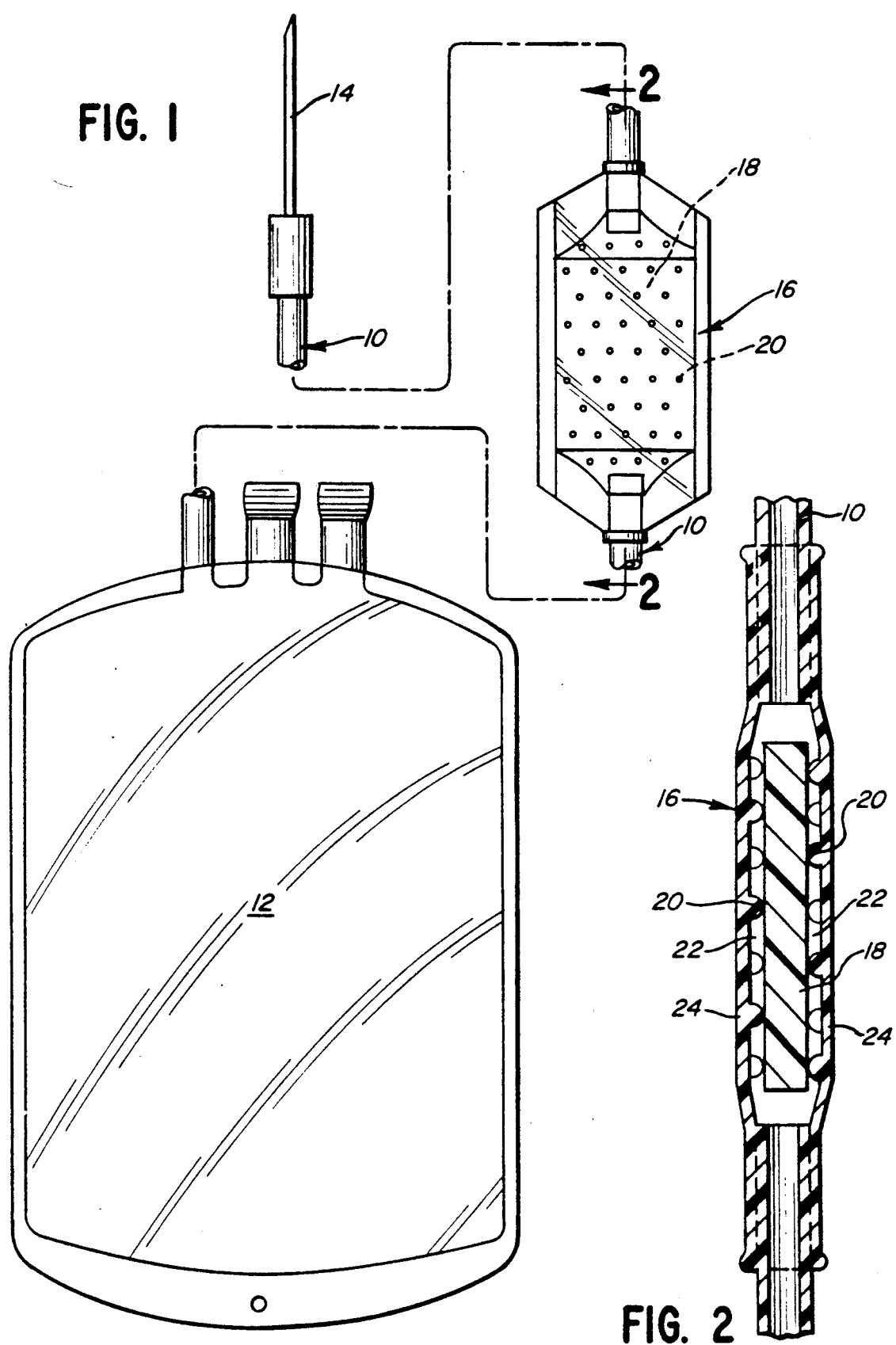

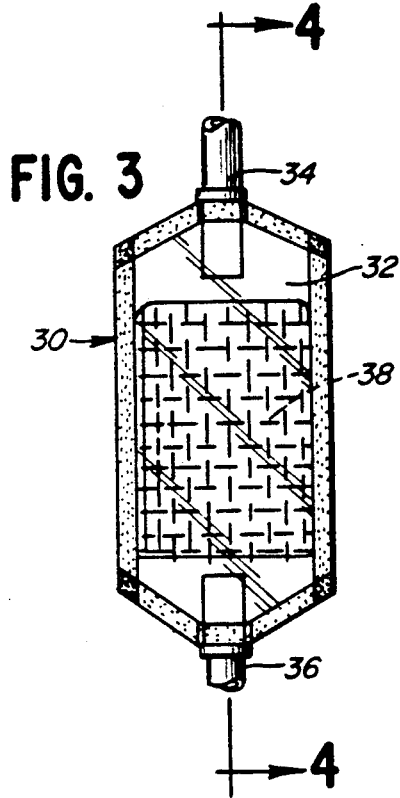
FIG. 3
FIG. 4
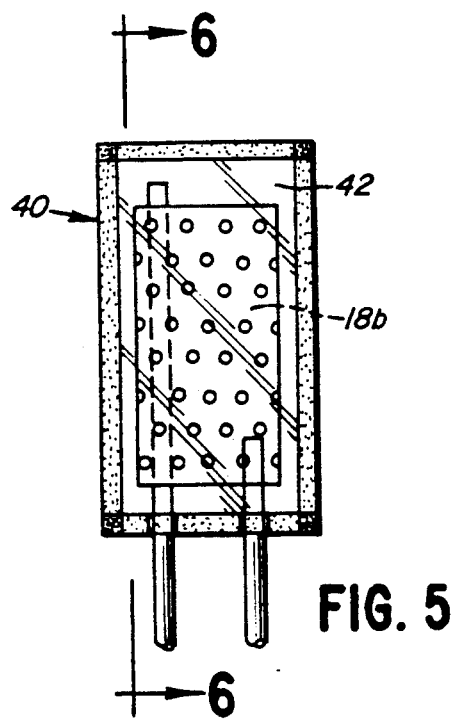
FIG. 5
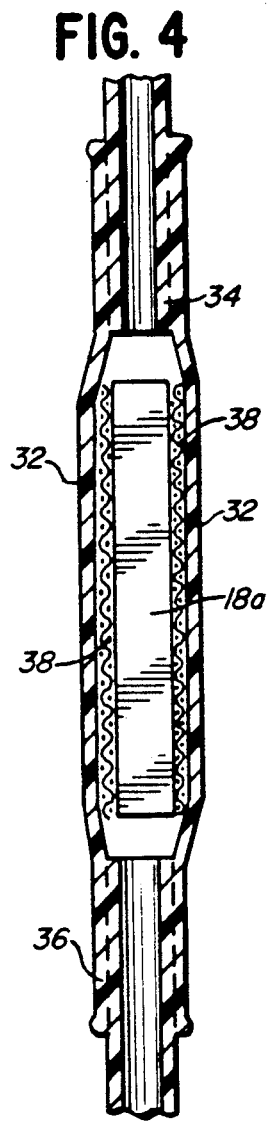
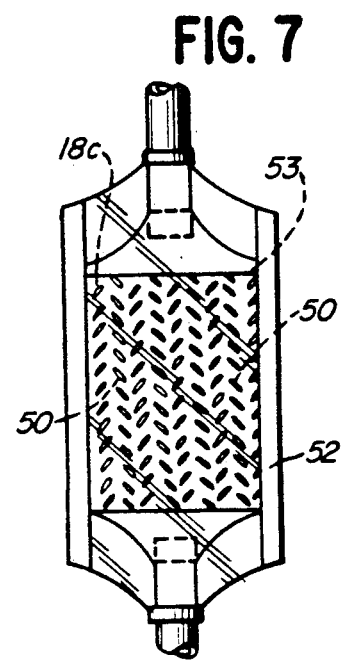
FIG. 7
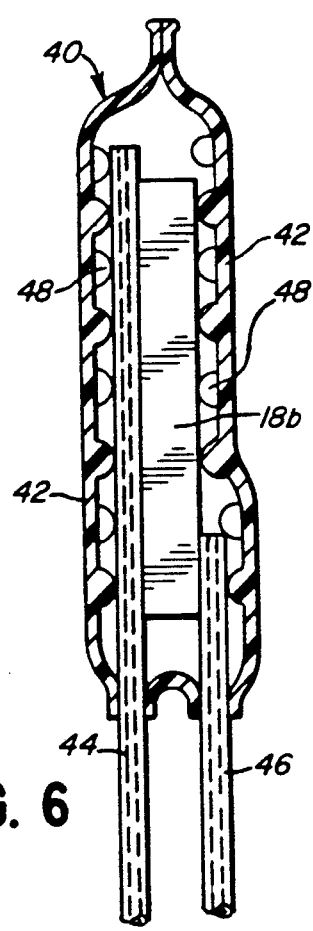
FIG. 6

AMPULE FOR CONTROLLED ADMINISTRATION OF BENEFICIAL AGENT

TECHNICAL FIELD

As blood is collected from the donor, it passes into a container such as a blood bag which contains an anticoagulant system. Such anticoagulant systems are typically a small amount of liquid solution which is stored in the bag, being typically ACD, CPD, CPD-adenine, or the like. Additionally, it has been suggested that the anticoagulant system may be placed as a dried coating on the interior of the blood collection container.

With these systems, as the blood is introduced into the container, the ratio of the whole blood present to the anticoagulant present is undesirably high, consequently producing a significant and detrimental osmotic imbalance. While this problem is quickly corrected with the addition of subsequent amounts of blood, it can be damaging to the first aliquot of blood cells administered into the collection bag.

Accordingly, there is a need for a blood handling system where beneficial agents such as anticoagulant/storage agents may be administered to the blood without the initial, undesirable osmotic effect that currently takes place at the beginning of the blood collection.

Additionally, in the manufacture of conventional blood storage bags which contain a liquid anticoagulant, a capital intensive and closely controlled manufacturing process is required, including a liquid filling operation (which requires a (clean room), batch steam sterilization procedures, and packaging of the blood bag in an additional moisture barrier container for storage. If it were possible to make use of blood bags which did not contain a liquid anticoagulant system, it would be possible to greatly simplify the manufacturing process, making use of radiation sterilization, and eliminating the additional moisture barrier packing which is currently necessary.

Additionally, blood storage bags which contain either a liquid anticoagulant or a dried coating thereof on the interior walls result in a container that must be completely filled with blood in order to be usable. If, for any reason, the donor is unable to donate one complete unit of blood, the entire, underfilled unit typically is not used, due to an excess concentration of anticoagulation agent present in the reduced volume of blood, since the anticoagulant present in the bag is intended for one complete unit of blood. If empty, anticoagulant-free blood storage bags were used in which the blood was still properly provided with anticoagulant/storage agents, these underfilled units could still be used for pediatric or partial transfusion purposes, and would not have to be discarded.

In a U.S. patent application Ser. No. 120,896 entitled Controlled Administration of Beneficial Agent to Blood, assigned to Baxter Travenol Laboratories, Inc. and filed on the same day as this present application, a technique and apparatus for solving the above problem is provided, to permit the application of a beneficial agent such as anticoagulant/storage agent to blood while the blood is passing through a conduit into a container. Thus, blood storage containers without any beneficial agent therein may be manufactured and used, for the significant manufacturing advantages described above. Additionally, partial units of blood may be collected and used.

As described in the patent application cited above, the beneficial agent may be carried in a conduit through which medical solution, typically blood, passes, typically on its way to a container. As it passes through the beneficial agent, a controlled amount of beneficial agent dissolves into each aliquot of medical solution which passes, with such controlled amount per aliquot being substantially uniform for all of the aliquots that pass from the first one to the last one. In accordance with this invention, improved uniformity of transfer of the beneficial agent to the various aliquots of medical solution may be obtained, along with desirable improvement in control and precision in the process.

In this invention, a flexible ampule member is provided which may be used in procedures as discussed above. The ampule is designed to naturally provide flow channels along its length, and, despite its flexibility, to remain open even in the presence of suction pressure on liquids passing through it. Additionally, significant improvements in constancy of the flow path size, and accordingly improved constancy of take-up of a beneficial agent carried within the ampule, can be achieved by this invention.

DESCRIPTION OF THE INVENTION

In this invention, a flexible ampule member defines a pair of opposed, flexible sides sealingly enclosing a space which contains a mass of beneficial agent which is soluble in aqueous solution. Inlet and outlet port means communicate between the space and the exterior of the ampule. By this invention, flow promoting means are positioned between the mass of beneficial agent at least one opposed, flexible side, to facilitate the formation of fluid flow paths along the path of beneficial agent.

For example, the flow promoting means may be inwardly extending projections which are integrally carried on the inner surfaces of opposed, flexible sides, being typically formed thereon as the flexible sheeting from which the sides are made is formed.

These inwardly extending projections may be bumps of substantially circular cross section, for example, or they may be ribs or ridges, if desired, or any other appropriate flow-promoting projections.

Alternatively, the flow promoting means may comprise at least one meshed member, for example, woven or non-woven plastic screening or the like, typically as a separate layer lying against the mass of beneficial agent. Alternatively, the meshed member may be part of the mass of beneficial agent, to define irregularities in the surface of the mass of beneficial agent to facilitate the formation of flow channels along such surface. As another alternative, the soluble material of the beneficial agent in the mass may be shaped to form ribs or projections on its surface so that the flow promoting means are an integral part of the mass of beneficial agent.

The mass of beneficial agent is preferably a unitary mass, for example, a tablet of glassy material which comprises at least one material from the group consisting of sugar and a water soluble, non-toxic citrate such as sodium citrate or citric acid. Typically, a mixture of sodium citrate and citric acid is used to provide the desired pH control in a manner dependent upon the proportions of such mixture.

One typical use of such a beneficial agent positioned within the flexible ampule of this invention is to serve as a preservative/anticoagulant for blood. Blood may be collected from a donor, for example, and passed through the ampule of this invention in a closed system to a storage container. As it passes through the ampule, the blood picks up from the mass of beneficial agent desired materials for its preservation and anticoagulation.

Any known anticoagulant formulation or other blood cell preservative, such as platelet preservatives, may be so incorporated into the mass of beneficial agent. For example, the mass of beneficial agent, particularly in its glassy form, may have a sugar such as glucose, which may also include a water soluble, non-toxic source of citrate as described above in sufficient concentration to have an anticoagulating effect on passing blood.

Additionally, a water soluble, non-toxic source of phosphate may be present in a concentration effective to promote blood storage in known manner. Adenine may be present, if desired, as well as any other ingredient which is desired for the storage of blood or components thereof.

By the term "blood" it is intended to include not only whole blood, but components of blood as may be desired, for example, blood plasma (either platelet rich or platelet poor) or suspensions of packed blood cells, white cells, or platelets in saline solution, any other appropriate suspension of blood cells, or the like.

The typical sugars which may be used in the mass of beneficial agent are, of course, soluble, nontoxic sugars which may or may not be metabolizable as a nutrient according to the desires of the formulator and the use to which the glassy mass of beneficial agent is to be put. Specifically, the sugar may be one or more of those selected from the group consisting of glucose, lactose, sorbitol and mannitol. A patent application filed simultaneously with this present patent application and entitled Glassy Sugar Matrix for Controlled Administration of Beneficial Agent Ser. No. 120,892 deals with the related area of how tablets of beneficial agent may be made and used in a soluble glassy form. The glassy characteristic of the tablet may be formulated through the presence of a sugar or a citrate as described above, with other beneficial ingredients being present as may be desired.

The ampule of this invention may be connected to one or more other tubular sets or containers, for example, to become part of a closed system for treatment of blood, or treatment of solutions to provide beneficial ingredients to them, which solutions then are administered to a patient. Alternatively, the ampule of this invention may be integrally and permanently connected to a set or container for the transfer and storage of aqueous medical solutions, including blood.

The use of a substantially dry mass of beneficial agent, positioned in an ampule in accordance with this invention, provides significant advantages. The significant advantages of the empty bag or the receptacle which thus may be used for blood or other medical solution have been described above. Additionally, transportation and handling advantages are achieved, when compared particularly with containers of frozen drug solution, which must be transported in frozen condition.

In many cases, in this invention, the drug for administration may be simply incorporated into the mass of beneficial agent. If desired, a parenteral solution such as saline may be passed over the mass of beneficial agent and directly into the patient, carrying a controlled amount of drug with it. Thus, critical drugs may be administered to a patient without a special, separate step of reformulation of the dry drug into the parenteral solution.

Thus, significant advantages of manufacturing, transportation, storage, and handling are provided in accordance with this invention.

Additionally, glassy materials of sugar and/or citrate having low water content (for example 1% to 2% by weight) are good oxygen barriers. Thus, oxygen sensitive drugs may be protected while incorporated in the glassy mass of beneficial agent which may be used in this invention. Additionally, the system of this invention is well suited for gamma irradiation sterilization, and moisture sensitive drugs are also protected by storage in the glassy mass of beneficial agent in accordance with this invention. It is believed that sugar and/or citrate present can exert a protective action on drugs or other effective agents which are mixed in the glassy mass with the sugar prior to contact with the medical solution for use, providing protection against moisture, oxygen, and even gamma radiation to reduce loss of effective agent during gamma irradiation during sterilization. Without wishing to be limited to any theory of operation of the invention, it is believed that hydroxyl groups present in the glassy mass can act as free-radical scavengers to protect sensitive effective agents present from degradation during or following gamma irradiation for sterilization.

Additionally, the glassy sugar masses which may be used in this invention are resistant to bacterial attack due to their low water content. It is generally preferred for the water content of such glassy masses to be about 1% to 2%, and typically no more than about 5% by weight.

Also, the glassy mass of this invention can be effectively molded during manufacture to form a tablet or tablets of desired dimension, to obtain an exact, desired dissolution rate as medical solution, such as blood, passes in contact therewith.

DESCRIPTION OF DRAWINGS

FIG. 1 is a plan view of a blood collecting set made in accordance with this invention, shown to be integrally connected to a blood storage bag.

FIG. 2 is a sectional view taken along line 2—2 of FIG. 1.

FIG. 3 is an elevational view of another embodiment of the ampule of this invention, which may be substituted for the ampule as shown in FIG. 1.

FIG. 4 is a sectional view taken along line 4—4 of FIG. 3.

FIG. 5 is an elevational view of yet another embodiment of flexible ampule in accordance with this invention, for uses where it is convenient for the flow inlet and outlet to come from the same end.

FIG. 6 is a sectional view taken along line 6—6 of FIG. 5.

FIG. 7 is an elevational view of another embodiment of a portion of the device of FIG. 1.

DESCRIPTION OF SPECIFIC EMBODIMENTS

Referring to FIGS. 1 and 2, there is shown a set 10 for collecting blood from a patient or other donor and conveying it to blood storage container 12, which may be made in substantially conventional manner. Set 10 carries at one end a conventional blood connection needle 14 for collecting blood from the venous system of the donor, which blood then passes through set 10 into blood bag 12.

In accordance with this invention, the conduit of set 10 defines an enlarged ampule portion 16 which includes a glassy, solid mass 18 of dry blood storage anticoagulant preparation, typically having a water content on the order of no more than about 2 percent by weight. Anticoagulant tablet 18 is shown to be made in the form of a thin, rectangular member positioned within enlarged portion 16.

In accordance with this invention, enlarged ampule portion 16 may be made of a pair of thermoplastic sheets such as polyvinylchloride, peripherally sealed together except at sealed inlet port 17 and outlet port 19. The inner surfaces of both walls 24 of ampule portion 16 define an array of small projections 20 which project inwardly to define flow passages 22 between walls 24 and the surface of anticoagulant preparation tablet 18.

Specifically, anticoagulant preparation tablet 18 may comprise, for example, a dried mixture of:

|  | Wt. % Present |
| --- | --- |
| Dextrose | 44 |
| Sodium Citrate | 46 |
| Citric Acid | 6 |
| Sodium Biphosphate | 4 |

To manufacture tablet 18, the above dextrose is dissolved as a near saturated solution in water by heating to boiling. Then water is removed by boiling under a vacuum of about 2 inches of mercury and up to about 295 F., until the dextrose reaches the desired water content of 2 weight percent or less (as defined by its temperature at the air pressure obtained by the vacuum system). The viscous mass is then cooled to avoid crystalization, to obtain a supercooled solution.

The other ingredients are added when the temperature of the molten dextrose falls to about 200 F., with vigorous stirring or alternatively in a twin screw extruder, to form a homogeneous mass. This material is molded into the desired shape and allowed to solidify, to form a white, glassy mass in the shape of tablet 18, which may be then sealed into portion 16. Blood bag 12 may be initially free of any anticoagulant. The entire system, including tablet 18, is typically radiation sterilizable, since it is substantially free of moisture. Additionally, no overpouch or other outer package is required to prevent the loss of water from a liquid anticoagulant present, which constitutes a significant advantage over the conventional present blood collection equipment.

For use, a conventional phlebotomy is made into a vein of a blood donor with needle 14, and the blood flows through conduit 10. As it flows, it enters enlarged ampule portion 16, where it flows in a pair of opposed flow paths 22 between the walls 24 of enlarged portion 16 and the flat surfaces of tablet 18. As the blood so flows, the substance of tablet 18 is dissolved away into the flow of blood at a relatively uniform rate of dissolution, so that each individual portion of the flowing blood passing through conduit 10 picks up a substantially similar amount of the dissolved substance of tablet 17 as it flows across it. From there, the flowing blood, carrying the dissolved anticoagulant, glucose, etc. passes into bag 12 for storage, without encoutering an excessive concentration of anticoagulant or other agent.

It is generally desirable for the tablet 18 to be of such a thickness that it is not completely eroded away by the time that the last of the blood has passed across it to fill bag 12 to its desired amount. When tablet 18 retains its basic rectangular shape to the end of the flow process, even though it becomes thinner, a relatively constant transfer of anticoagulant to all portions of the blood is achieved, particularly when the flow rate of the blood (or other solution) is relatively constant.

Other dry forms of beneficial agents, particularly anticoagulant/preservatives, may also be used as desired, as a substitute for the specific forms of beneficial agent illustrated above with respect to tablet 18.

Any design of blood bag or other container may also be utilized in accordance with this invention. If desired, the tablet 18 or an equivalent mixture of materials may be encapsulated and released via diffusion through a semipermeable membrane.

Additionally, the invention of this application may be used in conjunction with various other blood collection, separation, or handling procedures, for example plasma separation. Medications may be administered to blood in accordance with this invention by an apheresis procedure or the like.

Alternatively, an antibiotic or other drug may be mixed into the molten sugar or citrate mixture as described above when it is at a temperature of about 200 F.. After intimate mixing, the molten mixture is molded into tablet form, or any other desired shape, and allowed to solidify to a solid, glassy form. The resulting tablets may be placed into a chamber similar to enlarged portion 16 of set 10 which may be adapted for connection, or integrally connected with, a bag of parenteral solution. FIG. 1 in this circumstance can represent such a system, in which bag 12 contains, for example, sterile normal saline solution or even pure water, although such a system might not be fail safe since intravenously administered water is very damaging to blood cells.

In this instance, connection with the venous system of a patient is made by needle 14, and the parenteral solution in bag 12 is allowed to pass from bag 12 through set 10 into the patient's venous system. As it passes through enlarged ampule portion 16, the sugar and admixed drug of tablet 18 dissolves into the passing parenteral solution at a predetermined rate, so that the desired amount of drug may be administered simply by administering a desired quantity of parenteral solution from bag 12 at a predetermined rate of flow.

Thus, the invention of this application may not only be used for the handling of blood, but it may be used for the administration of drugs or other beneficial agents directly to the patient, or to another container in which solution from a bag is passed through a chamber which contains a glassy mass of sugar or citrate mixture, containing the desired beneficial agent. Such a system is very flexible as to the amount of beneficial agent which is delivered, contrary to many present systems. If one wishes to deliver only one third of the available beneficial agent in tablet 18, one can simply administer a predetermined amount of solution from bag 12 through set 10 to the patient, then terminating such administration when the desired amount of beneficial agent has been delivered.

Additionally, the enlarged chamber 16 may be manufactured in a form of a cartridge for connection to parenteral solution sets, with the various cartridges carrying different types of drugs as may be desired in the glassy mass of sugar or citrate. The doctor then needs to only select a cartridge which carries the drug of the desired type and concentration, and administer it to the patient without a special drug reconstitution step previous to the administration.

If desired, the glassy tablet of beneficial agent may comprise substantially no sugar, with the bulk of the glassy material being a non-toxic, water soluble citrate, for example, a mixture of sodium citrate and citric acid in appropriate proportions to provide the desired pH. This serves by itself as a carrier for drugs or the like, or, with blood, it serves as an anticoagulant.

Turning to FIGS. 3 and 4, an alternate design of flexible ampule is provided in accordance with this invention, for use in a manner similar to that previously described above with respect to ampule 16. Specifically, ampule 30 may be made of similar conventional construction from a pair of peripherally sealed thermoplastic sheets 32, with an inlet port 34 and an outlet port 36 extending through the seal line of sheet 32 for communication with the ampule interior. Within the ampule, a tablet 18a of beneficial material is provided. Tablet 18a may be of similar nature to the previously described tablet 18. The material of tablet 18 or 18a does not necessarily have to be in the glassy form as described above.

Additionally, a pair of small plastic screens 38 are positioned on each side of tablet 18a to provide space to flow channels between inlet 34 and outlet 36, which flow channels extend between tablet 18a and flexible walls 32 of ampule 30. Screens 38 also enhance fluid mixing in the flow channels. If desired, more than one screen may be placed on either side. Also, only one side of the ampule may have bumps or screening for a single flow path on only one side of the tablet.

While it is not necessary for the walls of the ampules of this invention to be flexible, such is preferred both for ease of construction, and also since, in that circumstance, it becomes possible to keep a fairly uniform flow path thickness along tablets 18 or 18a, even as the tablets themselves grow thinner through dissolution of their substance into passing fluid. In the case of a flexible-walled ampule such as ampule 16 or 30, particularly in the case where suction pressure is used, flexible walls 32 will be pressed inwardly against tablets 18 or 18a as the tablets erode and become thinner, so that there is essentially no difference in the thickness of the flow path extending across the respective tablets, with the result of improved uniformlty of take-up of beneficial agent in differing aliquots of fluid which pass across the respective tablets throughout the process.

Turning to FIGS. 5 and 6, a different design for the ampule of this invention is disclosed. In this case, ampule 40 once again may be made of a pair of peripherally sealed thermoplastic sheets 42 containing a tablet 18b of soluble beneficial agent. However in this case, inlet port 44 and outlet port 46 extend into the interior of ampule 40 from the same end. Inlet port 44 is then elongated as shown, so that entering fluid has to traverse substantially the entire length of ampule 40 before finding its way to outlet port 46. Thus, fluid extends along substantially the entire length of both sides of tablet 18b for dissolution thereof into the various aliquots of fluid in a substantially constant manner throughout the process, in a manner similar to the previous embodiments.

As shown in FIG. 6, each thermoplastic wall 42 defines on its inner surfaces a series of protrusions 48, in a manner similar to the embodiment of FIGS. 1 and 2, to provide a flow path for fluid. Alternatively, screening similar to screening 38 may be used, if desired.

As a further alternative, for any of the embodiments, the tablets 18, 18a, or 18b may be formulated with a roughened surface, so that the flow channel defining projections are provided by the tablet itself rather than by a separate member or the inner wall of the ampule. This may be accomplished either by molding the tablet itself, or by embedding screening or the like in the surface of the tablet so that at least portions of the screening project outwardly to form the desired flow channels.

FIG. 7 shows another alternative design for enlarged ampule portion 16, of identical design to ampule portion 16 except for a difference in the design of projections 50, positioned on the inside of each sidewall 52, 53 on opposite sides of tablet 18c. As shown, projections 50 are in a "herringbone" pattern, for improved flow characteristics with desirable turbulent mixing.

The above has been offered for illustrative purposes only, and is not intended to limit the scope of the invention of this application, which is as defined in the claims below.

That which is claimed is:

1. An ampule which defines a pair of opposed, flexible sides sealingly enclosing a space which contains a mass of beneficial agent which is soluble in aqueous solutions, inlet and outlet port means communicating between said space and the exterior, and flow promoting means positioned between the mass of beneficial agent and at least one opposed, flexible side to form a fluid flow path along said mass of beneficial agent.

2. The ampule of claim 1 in which said flow promoting means are inwardly extending projections integrally carried on the inner surfaces of said opposed, flexible sides.

3. The ampule of claim 2 in which said inwardly extending projections comprise bumps of substantially circular cross section.

4. The ampule of claim 1 in which said flow promoting means comprise at least one meshed member.

5. The ampule of claim 4 in which the meshed member is a separate layer of meshed material lying against said mass of beneficial agent.

6. The ampule of claim 1 in which said mass of beneficial agent is a unitary mass of glassy material comprising at least one material selected from the group consisting of sugar and a water soluble, non-toxic citrate.

7. The ampule of claim 1 in which said flow promoting means includes means for enhancing mixing of the beneficial agent with fluid entering said ampule.

8. An ampule which defines a pair of opposed, flexible sides sealingly enclosing a space which contains a mass of beneficial agent which is soluble in aqueous solution, inlet and outlet port means communicating between said space and the exterior, said opposed, flexible sides defining inwardly extending projections carried on the inner surfaces thereof to serve as flow promoting means, to form flow paths along both sides of said mass of said beneficial agent, said mass of beneficial agent being a unitary mass of glassy material comprising at least one material selected from the group consisting of sugar and a water soluble, non-toxic citrate.

9. The ampule of claim 8 in which said inwardly extending projections comprises bumps of substantially circular cross section.

10. A method of administering a beneficial agent which comprises passing an aqueous solution between a pair of opposed, flexible sides of an ampule member and a mass of beneficial agent contained in said ampule and which is soluble in said aqueous solution, maintaining said opposed, flexible sides a substantially constant depth from said mass of beneficial agent by defining inwardly extending projections on the inner surfaces of said opposed flexible sides to serve as flow promoting means to press against said mass of beneficial agent to facilitate the formation of flow paths along both sides of said mass of beneficial agent, whereby when a less than atmospheric pressure is imposed on the aqueous solution flowing through said ampule, as said mass of beneficial agent erodes by dissolution into the aqueous solution, the opposed flexible sides maintain said depth of said flow paths.

11. The method of claim 10 in which said inwardly extending projections comprise bumps of substantially circular cross-section.

12. The method of claim 10 in which said mass of beneficial agent is a unitary mass of glassy material comprising at least one material selected from the group consisting of sugar and a water soluble, non-toxic citrate.

13. An ampule which defines a pair of opposed, flexible sides sealingly enclosing a mass of beneficial agent which is soluble in aqueous solution, inlet and outlet port means communicating between said space and the exterior, and means for maintaining a flow path of substantially constant thickness between at least one of said sides and said mass of beneficial agent as said mass of beneficial agent is dissolved away by solution passing through said inlet and outlet port means and flowing through said flow path.

14. The ampule of claim 13 in which said flow path maintaining means includes inwardly extending projections integrally carried on the inner surfaces of said opposed, flexible sides, said ampule being connected to means for imposing a suction pressure on said flow path.

15. The ampule of claim 13 in which said flow path maintaining means includes at least one meshed member positioned in said flow path, said ampule being connected to means for imposing a suction pressure on said flow path.

* * * * *